US010984341B2

(12) United States Patent
Dubovsky et al.

(10) Patent No.: US 10,984,341 B2
(45) Date of Patent: Apr. 20, 2021

(54) DETECTING COMPLEX USER ACTIVITIES USING ENSEMBLE MACHINE LEARNING OVER INERTIAL SENSORS DATA

(71) Applicant: International Business Machines Corporation, Armonk, NY (US)

(72) Inventors: Oded Dubovsky, Haifa (IL); Alexander Zadorojniy, Haifa (IL); Sergey Zeltyn, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 841 days.

(21) Appl. No.: 15/716,524

(22) Filed: Sep. 27, 2017

(65) Prior Publication Data

US 2019/0095814 A1 Mar. 28, 2019

(51) Int. Cl.
*G06N 20/00* (2019.01)
*G06F 1/16* (2006.01)
(Continued)

(52) U.S. Cl.
CPC ............ *G06N 20/00* (2019.01); *A61B 5/1114* (2013.01); *A61B 5/1118* (2013.01);
(Continued)

(58) Field of Classification Search
CPC ...... G06N 20/00; G06N 7/005; G06N 99/005; G06F 1/163; G06F 3/011; G06F 3/017;
(Continued)

(56) References Cited

U.S. PATENT DOCUMENTS

2015/0109202 A1\* 4/2015 Ataee ................... A61B 5/0488
345/156
2015/0127298 A1\* 5/2015 Gangumalla ........ A61B 5/1123
702/160
(Continued)

OTHER PUBLICATIONS

Zeltyn et al., "Enhanced sliding window approach for the inertial-based activity recognition", IUI 2016 Workshop: A joint Workshop on Smart Connected and Wearable Things, Mar. 10, 2016, Sonoma, CA, USA. (Year: 2016).\*
(Continued)

*Primary Examiner* — Dave Misir
(74) *Attorney, Agent, or Firm* — G. E. Ehrlich (57) ABSTRACT

A computer implemented method of detecting complex user activities, comprising using processor(s) in each of a plurality of consecutive time intervals for: obtaining sensory data from wearable inertial sensor(s) worn by a user, computing an action score for continuous physical action(s) performed by the user, the continuous physical action(s) extending over multiple time intervals are indicated by repetitive motion pattern(s) identified by analyzing the sensory data, computing a gesture score for brief gesture(s) performed by the user, the brief gesture(s) bounded in a single basic time interval is identified by analyzing the sensory data, aggregating the action and gesture scores to produce an interval activity score of predefined activity(s) for a current time interval, adding the interval activity score to a cumulative activity score accumulated during a predefined number of preceding time intervals and identifying the predefined activity(s) when the cumulative activity score exceeds a predefined threshold.

15 Claims, 2 Drawing Sheets

(51) Int. Cl.
*G06N 7/00* (2006.01)
*A61B 5/11* (2006.01)
*G06F 3/01* (2006.01)
*A61B 5/00* (2006.01)
*G16H 50/20* (2018.01)
*G06F 3/0346* (2013.01)

(52) U.S. Cl.
CPC .......... *A61B 5/1126* (2013.01); *A61B 5/6802* (2013.01); *A61B 5/7246* (2013.01); *A61B 5/7264* (2013.01); *G06F 1/163* (2013.01); *G06F 3/011* (2013.01); *G06F 3/017* (2013.01); *G06N 7/005* (2013.01); *A61B 5/6814* (2013.01); *A61B 5/6823* (2013.01); *A61B 5/6824* (2013.01); *A61B 5/6828* (2013.01); *A61B 2562/0219* (2013.01); *G06F 3/0346* (2013.01); *G16H 50/20* (2018.01)

(58) Field of Classification Search
CPC .... G06F 3/0346; A61B 5/1114; A61B 5/1118; A61B 5/1126; A61B 5/6802; A61B 5/7246; A61B 5/7264; A61B 5/6814; A61B 5/6823; A61B 5/6824; A61B 5/6828; A61B 2562/0219; G16H 50/20
USPC .......................................................... 706/12
See application file for complete search history.

(56) References Cited

U.S. PATENT DOCUMENTS

| | | | |
|---|---|---|---|
| 2016/0074706 A1* | 3/2016 | Morris | A63B 24/0062 434/247 |
| 2017/0220122 A1* | 8/2017 | Raffa | G06F 1/1694 |
| 2017/0232294 A1* | 8/2017 | Kruger | G06F 19/00 434/247 |

OTHER PUBLICATIONS

Wang et al., "Real-time Activity Recognition in Wireless Body Sensor Networks: From Simple Gestures to Complex Activities", The Sixteenth IEEE International Conference on Embedded and Real-Time Computing Systems and Applications, 2010. (Year: 2010).*

Alam et al., "GeSmart: A Gestural Activity Recognition Model for Predicting Behavioral Health", SMARTCOMP 2014. (Year: 2014).*

Lara et al., "A Survey on Human Activity Recognition using Wearable Sensors", IEEE Communications Surveys & Tutorials, vol. 15, No. 3, Third Quarter 2013. (Year: 2013).*

Attal et al., "Physical Human Activity Recognition Using Wearable Sensors", Sensors 2015. (Year: 2015).*

* cited by examiner

DETECTING COMPLEX USER ACTIVITIES USING ENSEMBLE MACHINE LEARNING OVER INERTIAL SENSORS DATA

BACKGROUND

The present invention, in some embodiments thereof, relates to detecting complex user activities, and, more specifically, but not exclusively, to detecting complex user activities by aggregating detections of continuous physical actions and brief gestures characterizing the complex user activities.

Real-time recognition of human activities constitutes a challenging and practically important class of research problems. Applications which may benefit of such real-time human activities recognition may extend over a wide range including, for example, industrial safety, elder care, public security, health care, driving safety, and many more.

As wearable acceleration sensors are rapidly spreading for common use in a plurality of applications, the acceleration information obtained from such sensors may be used for recognizing the human activities in real time.

SUMMARY

According to a first aspect of the present invention there is provided a computer implemented method of detecting complex user activities comprising a plurality of continuous physical actions and brief gestures, comprising using one or more processors in each of a plurality of consecutive time intervals for:

Obtaining sensory data from wearable inertial sensor(s) worn by a user.

Computing an action score for one or more continuous physical actions performed by the user. The continuous physical action(s) extends over multiple basic time intervals and is indicated by one or more repetitive motion patterns identified by analyzing the sensory data.

Computing a gesture score for one or more brief gestures performed by the user. The brief gesture(s) is bounded in a single basic time interval and is identified by analyzing the sensory data.

Aggregating the action score and the gesture score to produce an interval activity score of one or more predefined activities of the user for a respective one of the plurality of consecutive time interval.

Adding the interval activity score to a cumulative activity score of the predefined activity(s) accumulated during a predefined number of preceding time intervals.

Identifying the predefined activity(s) when the cumulative activity score exceeds a predefined threshold.

Since by definition, complex activities of the users may comprise several physical actions—basic actions and/or gestures, in particular, long terms continuous actions and short term brief gestures, estimating the physical actions of the user(s) in both short term and long term time durations and aggregating the two time domains may significantly improve an accuracy of estimating the complex activity the user is currently involved in.

According to a second aspect of the present invention there is provided a system for detecting complex user activities comprising a plurality of continuous physical actions and brief gestures, comprising one or more processors adapted to execute code in each of a plurality of consecutive time intervals, the code comprising:

Code instructions to obtain sensory data from wearable inertial sensor(s) worn by a user.

Code instructions to compute an action score for one or more continuous physical actions performed by the user. The continuous physical action(s) extends over multiple basic time intervals and is indicated by one or more repetitive motion patterns identified by analyzing the sensory data.

Code instructions to compute a gesture score for one or more brief gestures performed by the user. The brief gesture(s) is bounded in a single basic time interval and is identified by analyzing the sensory data.

Code instructions to aggregate the action score and the gesture score to produce an interval activity score of one or more predefined activities of the user for a respective one of the plurality of consecutive time interval.

Code instructions to add the interval activity score to a cumulative activity score of the predefined activity(s) accumulated during a predefined number of preceding time intervals.

Code instructions to identify the predefined activity(s) when the cumulative activity score exceeds a predefined threshold.

According to a third aspect of the present invention there is provided a computer program product for detecting complex user activities comprising a plurality of continuous physical actions and brief gestures, comprising:

A non-transitory computer readable storage medium.

First code instructions for obtaining sensory data from wearable inertial sensor(s) worn by a user.

Second code instructions for computing an action score for one or more continuous physical actions performed by the user. The continuous physical action(s) extends over multiple basic time intervals and is indicated by one or more repetitive motion patterns identified by analyzing the sensory data.

Third code instructions for computing a gesture score for one or more brief gestures performed by the user. The brief gesture(s) is bounded in a single basic time interval and is identified by analyzing the sensory data.

Fourth code instructions for aggregating the action score and the gesture score to produce an interval activity score of one or more predefined activities of the user for a respective one of the plurality of consecutive time interval.

Fifth code instructions for adding the interval activity score to a cumulative activity score of the predefined activity(s) accumulated during a predefined number of preceding time intervals.

Sixth code instructions for identifying the predefined activity(s) when the cumulative activity score exceeds a predefined threshold.

Wherein the first, second, third, fourth, fifth and sixth program instructions are executed by one or more processors from the non-transitory computer readable storage medium.

In a further implementation form of the first, second and/or third aspects, one or more of the wearable inertial sensor(s) is an accelerometer located and configured to measure an acceleration of one or more members of a group consisting of: the user, a head of the user and one or more limb of the user. The use of accelerometers is rapidly increasing for a plurality of user wearable applications. Therefore, using such accelerometers may allow for simple, flexible and/or cost effective deployment, adaptation and/or use. Moreover, in some case where the accelerometer(s) are already deployed (worn by the user), the acceleration sensory data may already be available thus significantly simplifying the system and reducing cost and/or effort for collecting the acceleration sensory data.

In a further implementation form of the first, second and/or third aspects, one or more of the wearable inertial sensor(s) is a gyroscope located and configured to measure an angular velocity of one or more members of a group consisting of: the user, a head of the user and one or more limb of the user. The use of gyroscopes is rapidly increasing for a plurality of user wearable applications. Therefore, using such gyroscopes may allow for simple, flexible and/or cost effective deployment, adaptation and/or use. Moreover, in some case where the gyroscope(s) are already deployed (worn by the user), the acceleration sensory data may already be available thus significantly simplifying the system and reducing cost and/or effort for collecting the acceleration sensory data.

In a further implementation form of the first, second and/or third aspects, the one or more continuous physical actions are identified using one or more action detection algorithms. One or more of the action detection algorithm(s) implement a decision tree algorithm. Applying the action detection algorithm(s) may significantly improve the estimation accuracy of the basic action(s) of the user since the trained activity detection algorithm(s) may evolve over time as more data is collected for more basic actions and/or for more users.

In a further implementation form of the first, second and/or third aspects, the action detection algorithm(s) are trained with a training dataset relating to the one or more continuous physical actions. Training the action detection algorithm(s) with training data relating to the continuous physical actions may significantly improve the ability of the action detection algorithm(s) to detect such continuous physical actions.

In a further implementation form of the first, second and/or third aspects, the action score is computed according to an action probability value associated with the one or more continuous physical actions. The probability value which may typically be provided by the action detection algorithm(s) may be essential to accurately evaluate certainty, reliability and/or variation of the detection of the continuous physical action(s) the user is estimated to perform during the current time interval.

In an optional implementation form of the first, second and/or third aspects, a weight is assigned to the probability value for computing the action score. Assigning a weight may allow adjusting the contribution of the respective detected continuous physical action to the overall estimation of the complex activity the user is estimated to be currently involved in.

In a further implementation form of the first, second and/or third aspects, the one or more brief gestures are identified using one or more gesture detection algorithms. One or more of the gesture detection algorithms implement a Hidden Markov Model (HMM) algorithm. Applying the gesture detection algorithm(s) may significantly improve the estimation accuracy of the gesture(s) of the user since the trained gesture detection algorithm(s) may evolve over time as more data is collected for more gestures and/or for more users.

In a further implementation form of the first, second and/or third aspects, the gesture detection algorithm(s) are trained with a training dataset relating to the one or more brief gestures. Training the gesture detection algorithm(s) with training data relating to the gestures may significantly improve the ability of the action detection algorithm(s) to detect such gestures.

In a further implementation form of the first, second and/or third aspects, the gesture score is computed according to a gesture probability value associated with the one or more brief gestures. The probability value which may typically be provided by the gesture detection algorithm(s) may be essential to accurately evaluate certainty, reliability and/or variation of the detection of the gesture(s) the user is estimated to perform during the current time interval.

In an optional implementation form of the first, second and/or third aspects, a weight is assigned to the probability value for computing the gesture score. Assigning a weight may allow adjusting the contribution of the respective detected gesture to the overall estimation of the complex activity the user is estimated to be currently involved in.

In a further implementation form of the first, second and/or third aspects, the interval activity score is aggregated using an aggregation algorithm trained using machine learning. Applying the machine learning based aggregation algorithm may significantly improve the estimation accuracy of the complex activity(s) the user is currently involved in. The trained aggregation algorithm may evolve over time as more data is collected for more complex activities session and/or for more users.

In a further implementation form of the first, second and/or third aspects, the aggregation algorithm is trained with a training dataset relating to the activity score and the gesture score. Using the training dataset, the trained aggregation algorithm may learn the correlation between the long terms continuous actions and short term brief gestures and may therefore improve the estimation accuracy over time and/or based on extended training dataset(s).

In a further implementation form of the first, second and/or third aspects, the plurality of consecutive time intervals form an activity period implementing a sliding time window in which after each time interval a new time interval is added to the activity period and an earliest time interval is discarded from the activity window. Applying a sliding window allows continuous tracking of the user actions and gestures to identify the complex activity(s) over continuous time frames as opposed to discrete time frames in which identified continuous physical actions and/or gestures, in particular prolonged basic actions may be difficult to correlate with each other.

In a further implementation form of the first, second and/or third aspects, the cumulative activity score is reset in case the predefined activity is identified. Resetting the activity score is required to start over the complex activity detection process after discarding the contribution of the already detected complex activity of the same type.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced In the drawings.

DETAILED DESCRIPTION

The present invention, in some embodiments thereof, relates to detecting complex user activities, and, more specifically, but not exclusively, to detecting complex user activities by aggregating detections of continuous physical actions and brief gestures characterizing the complex user activities.

According to some embodiments of the present invention, there are provided methods, systems and computer program products for detecting one or more predefined complex activities, for example, eating, cooking, studying, lecturing, attending a meeting, working and/or the like performed by one or more users. The detection is based on applying an ensemble of machine learning algorithms for estimating different aspects of the user's physical activity(s) and/or action(s) as captured by one or more wearable acceleration sensors, in particular long term continuous actions and short term brief gestures. A machine learning based aggregation may then be applied for aggregating and/or correlating one or more basic continuous physical actions estimated to be performed by the user(s) and one or more brief gestures estimated to be performed by the user(s) during a predefined period of time. Each of the complex activities may be predefined in advance to include one or more of the basic continuous physical actions and one or more of the brief gestures, such that the combined (aggregated) estimation may be compared to the predefined complex activity(s) to determine if and which of the predefined complex activity(s) is performed by the user(s).

The physical actions and the gestures are identified by analyzing sensory data, in particular inertial sensory data received from one or more inertial sensors attached, worn and/or carried by the user. The inertial sensory data may include, for example, 3-axis acceleration, acceleration, deceleration, angular velocity, velocity, angular direction and/or the like of the user(s) and/or one or more parts thereof, for example, the head, a limb (a hand, a leg) to which the inertial sensor(s) is attached, worn and/or carried.

The sensory data may be collected for a plurality of basic time intervals, typically small. A predefined number of consecutive time intervals may be defined as a (complex) activity period which may be regarded as a sliding window advancing in time and comprising the predefined number of consecutive time intervals. The continuous basic continuous physical actions may be defined as prolonged, long term physical actions extending over a plurality of basic time intervals while the brief gestures may be defined as short term actions having a time duration which may typically be bounded within a single basic time interval. Identify the continuous basic continuous physical actions may be done based on analysis of the inertial sensory data during the basic time intervals. However detection of the basic continuous physical actions by analyzing the inertial sensory data may be done in consecutive time intervals which may differ in duration from the basic time intervals used to detect the gestures.

For each of the (basic) time intervals, one or more detection algorithms as known in the art may be applied to identify the basic continuous physical actions and/or the gestures performed by the user during the respective time interval. In particular, one or more of the detection algorithms, for example, a decision tree, a neural network, a random forest, a Support Vector Machine (SVM) and/or the like may be applied to analyze the acceleration sensory data to identify one or more repetitive motion patterns performed by the user which may be indicative of one or more of the basic continuous physical actions, for example, walking, running, going upstairs, going downstairs and/or the like. In parallel, one or more of the detection algorithms, for example, a Hidden Markov Model (HMM), a neural network, a decision tree, a random forest, an SVM and/or the like may be applied to analyze the acceleration sensory data to identify one or more of the brief gestures performed by the user, for example, a handshake, raising a glass, lifting a load and/or the like. Typically, one or more of the basic continuous physical actions and/or brief gestures are associated with a respective probability value assigned by the detection algorithm(s) to reflect a confidence level of the detection of the associated continuous physical action and/or gesture.

Based on the probability scores, a respective action score and a respective gesture score are computed for each of the basic continuous physical actions and/or brief gestures identified during the respective time interval. The action score(s) and gesture score(s) may be aggregated to compute an interval activity score for one or more predefined complex activities for the respective time interval. The aggregation may be done using an aggregation algorithm which employs machine learning trained using a plurality of sets of action score(s) and gesture score(s) where each of the sets may be associated with a label indicating one of the predefined complex activity(s).

Each computed interval activity score may be added, for example, combined, summed, aggregated and/or the like with a respective cumulative activity score accumulated for a respective one of the complex activity(s) during preceding time intervals of the activity period, i.e. during the sliding window associated with the respective complex activity(s).

In case the respective cumulative activity score exceeds a predefined threshold, the respective complex activity is identified and an identification indication may be generated. Following the identification, the respective cumulative activity score may be reset (i.e. zeroed) for the identified respective complex activity(s) before repeating the process 100 to identify additional complex activity(s).

Aggregating and/or correlating the basic continuous physical action(s) and the brief gesture(s) performed by the user during the activity period to identify the predefined complex activity of the user may present significant advantages over currently existing methods for identifying complex human activities. By definition, every complex activity conducted by users comprises several physical actions, meaning that each complex activity may be characterized by more basic actions and/or gestures, in particular, long terms continuous actions and short term brief gestures. Therefore, estimating the physical actions of the user(s) in both short term and long term time durations and aggregating the two time domains may significantly improve an accuracy of estimation of the complex activity the user(s) is currently involved in. Applying the sliding window activity period may allow continuously tracking the user actions and/or gestures to identify the complex activity(s) over continuous time frames. This is in contracts to using discrete time frames in which identified actions and/or gestures, in particular prolonged basic actions may be difficult to correlate with each other.

Moreover, applying a machine learning based aggregation algorithm may significantly improve the estimation accuracy as the aggregation algorithm may be trained and may further evolve over time as more data is collected for more complex activities session and/or for more users. The trained aggregation algorithm may learn the correlation between the long terms continuous actions and short term brief gestures and may therefore improve the estimation accuracy over time and/or based on extended training dataset(s). Experiments for detecting an eating complex activity have presented an improvement of over 5% in the detection accuracy compared to the currently existing methods.

Furthermore, as wearable acceleration sensors are becoming more common and their use is continuously growing, the acceleration sensory information provided by such wearable acceleration sensors may be already available for the activity detection mechanism thus avoiding the need to deploy application specific wearable acceleration sensors.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
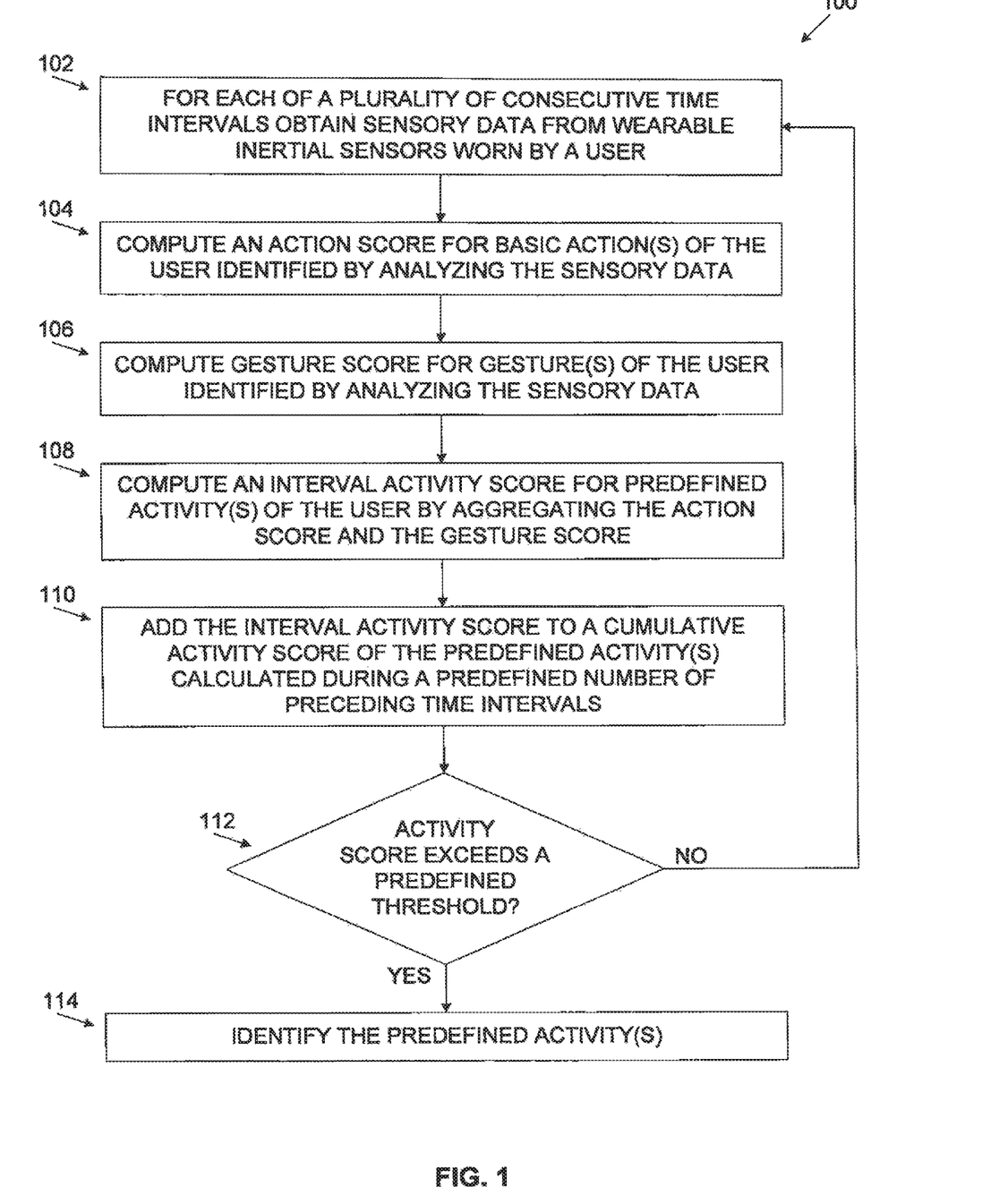
FIG. 1 is a flowchart of an exemplary process of detecting user activities comprising a plurality of continuous physical actions and brief gestures, according to some embodiments of the present invention.

Referring now to the drawings, FIG. 1 is a flowchart of an exemplary process of detecting user activities comprising a plurality of continuous physical actions and brief gestures, according to some embodiments of the present invention. A process 100 may be executed to detect one or more predefined complex activities, for example, eating, cooking, studying, lecturing, attending a meeting, working and/or the like performed by one or more users by correlating (aggregating) between one or more basic continuous physical actions performed by a user and one or more brief gestures performed by the user(s) during a predefined activity period. Each of the predefined complex activities is predefined to comprise a set of one or more of the basic continuous physical actions and one or more of the brief gestures. The physical actions and the gestures are identified by analyzing sensory data, in particular inertial sensory data received from one or more inertial sensors attached, worn and/or carried by the user.

The sensory data may be collected for a plurality of basic time intervals, typically small. A predefined number of consecutive time intervals may be defined as the (complex) activity period which may be regarded as a sliding window comprising the predefined number of consecutive time intervals.

For each of the (basic) time intervals, one or more detection algorithms as known in the art may be applied to identify the basic continuous physical actions and/or the gestures performed by the user. In particular, one or more of the detection algorithms, for example, a decision tree, a neural network, a random forest, an SVM and/or the like may be applied to analyze the sensory data to identify one or more repetitive motion patterns performed by the user which may be indicative of one or more of the basic continuous physical actions, for example, walking, running, going upstairs, going downstairs and/or the like. In parallel, one or more of the detection algorithms, for example, an HMM, a neural network, a decision tree, a random forest, an SVM and/or the like may be applied to analyze the sensory data to identify one or more of the brief gestures performed by the user. Typically, one or more of the basic continuous physical actions and/or brief gestures are associated with a respective probability value assigned by the detection algorithm(s) to reflect a confidence level of the detection of the associated continuous physical action and/or gesture. Identify the continuous basic continuous physical actions may be done based on analysis of the inertial sensory data during the basic time intervals. However detection of the basic continuous physical actions by analyzing the inertial sensory data may be done in consecutive time intervals which may differ in duration from the basic time intervals used to detect the gestures.

Using the probability scores, a respective action score and a respective gesture score are computed for each of the identified basic continuous physical actions and/or brief gestures. The action score(s) and gesture score(s) may be aggregated to compute an interval activity score for one or more predefined complex activities for the respective time interval. The computed interval activity score may be added, for example, combined, summed, aggregated and/or the like with a cumulative activity score accumulated for one or more of the complex activities during preceding time intervals of the activity period, i.e. the sliding window associated with the respective complex activity(s).

In case the cumulative activity score exceeds a predefined threshold, the respective complex activity is identified and an identification indication may be generated. Following the identification, the respective cumulative activity score may be reset (i.e. zeroed) before repeating the process 100 to identify additional complex activity(s).

Figure 2:
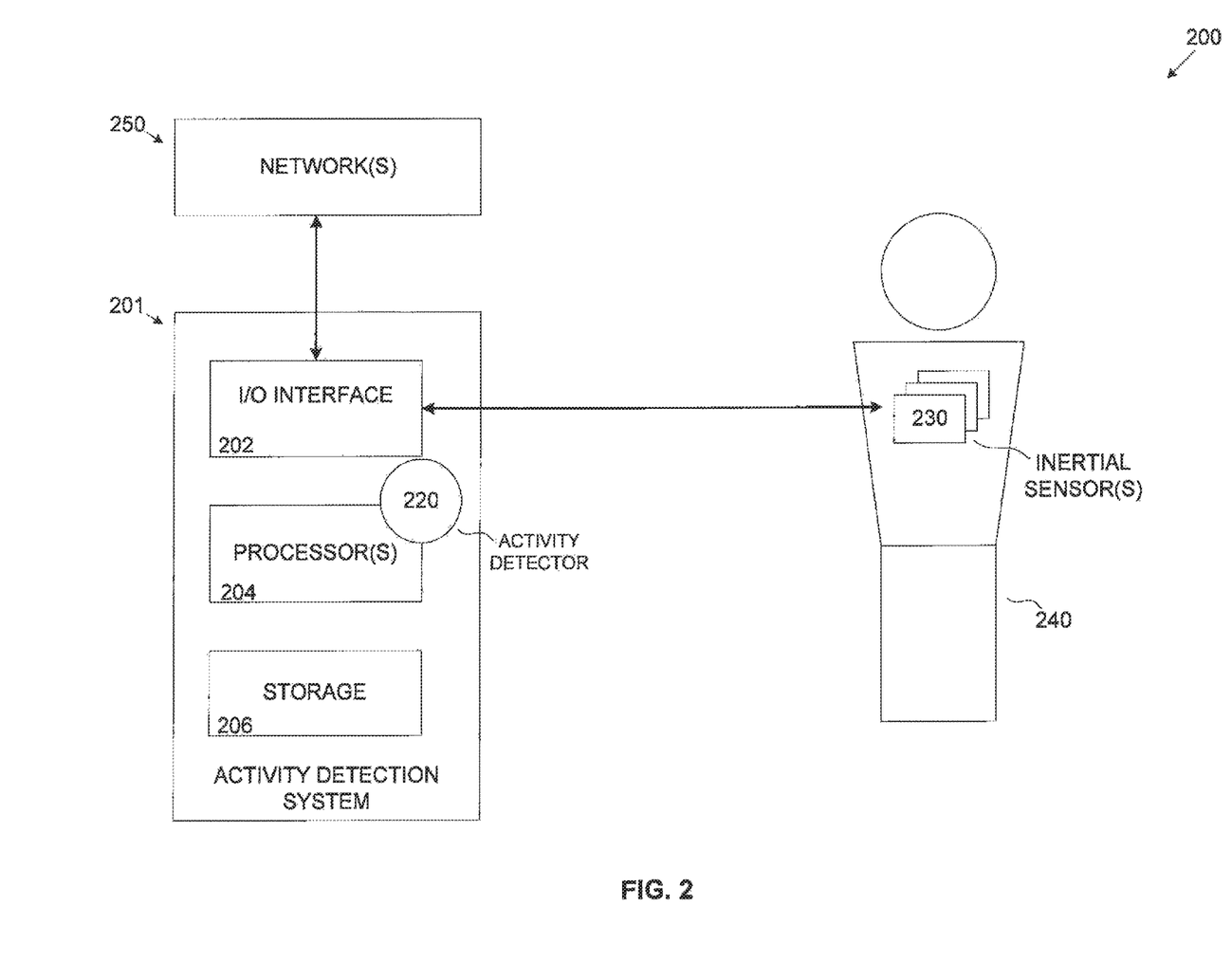
FIG. 2 is a schematic illustration of an exemplary system for detecting user activities comprising a plurality of continuous physical actions and brief gestures, according to some embodiments of the present invention.

Reference is also made to FIG. 2, which is a schematic illustration of an exemplary system for detecting user activities comprising a plurality of continuous physical actions and brief gestures, according to some embodiments of the present invention. An exemplary system 200 for identifying one or more of the complex activities performed by the user(s) includes an activity detection system 201, for example, a processing node, a computer, a laptop, a server, a mobile device (e.g. a tablet, a cellular device, a Smartphone, etc.), and/or any processing device having one or more processor. The activity detection system 201 comprises an Input/Output (I/O) interface 202 for connecting to one or more inertial sensors 230 worn by one or more users 240, a processor(s) 204 and storage 206. The processor(s) 204, homogenous or heterogeneous, may include one or more processors arranged for parallel processing, as clusters and/or as one or more multi core processor(s). The storage 206 may include one or more non-transitory persistent storage devices, for example, a hard drive, a Flash array and/or the like. The storage 206 may further comprise one or more network storage devices, for example, a storage server, a network accessible storage (NAS), a network drive, and/or the like. The storage 206 may also include one or more volatile devices, for example, a Random Access Memory (RAM) component and/or the like.

The storage 206 may store one or more software modules, for example, an OS, an application, a tool, an agent, a service, a script and/or the like each comprising a plurality of program instructions that may be executed by the processor(s) 204 from the storage 206. For example, the processor(s) 204 may execute an activity detector 220 for identifying one or more complex activities conducted by one or more of the users 240.

The inertial sensor(s) 230, for example, an accelerometer, a gyroscope, an Inertial Measurement Unit (IMU) and/or the like may be located and configured to provide acceleration sensory data for the user(s) 240. The inertial sensor(s) 230 may be attached, worn and/or carried by the user(s) 240 to provide the acceleration sensory data, for example, acceleration, deceleration, angular velocity, velocity, angular direction and/or the like of the user(s) 240 and/or one or more parts thereof, for example, the head of the user(s) 240, a limb (a hand, a leg) of the user(s) 240. For example, a certain inertial sensor 230 may be attached to a wrist of a certain user 240 to provide the acceleration sensory data measured for the hand of the certain user 240. In another example, a certain inertial sensor 230 may be attached and/or integrated in a hat worn by a certain user 240 to provide the acceleration sensory data measured for the head of the certain user 240. In another example, a certain inertial sensor 230 may be attached to a shirt and/or a body of a certain user 240 to provide the acceleration sensory data measured for the certain user 240 himself.

The inertial sensor(s) 230 may include one or more communication interfaces for communicating with the activity detection system 201 through one or more interfaces provided by the I/O interface 202, in particular, wireless interfaces, for example, a Radio Frequency (RF) interface, a Bluetooth interface, a Wireless LAN (WLAN, e.g. Wi-Fi) interface and/or the like.

The I/O interface 202 may further include one or more wired and/or wireless network interfaces, for example, a Local area Network (LAN) interface, a wide Area Network (WAN) interface, a cellular interface and/or the like to connect to one or more networks 250, for example, a LAN, a WAN, a Metropolitan Area Network (MAN) and/or the internet to facilitate communication with more or more remote locations and/or resources Optionally, the monitoring system 201 is utilized by one or more remote platforms, for example, a remote server, a cloud computing platform, such as, for example, Amazon Web Service (AWS), Google Cloud, Microsoft Azure and/or the like. Additionally, and/or alternatively, the monitoring application 220 may be implemented as one or more remote services, a remote service, a cloud service, Software as a Service (SaaS), a Platform as a Service (PaaS) and/or the like. In such scenarios, the inertial sensor(s) 230 may be configured, adapted and/or designed to transmit the acceleration sensory data to the remote platform(s) and/or the remote service(s) through one or more networks such as the network(s) 250. Additionally and/or alternatively, the inertial sensor(s) 230 may be configured, adapted and/or designed to communicate with one or more intermediate devices, for example, a mobile device (e.g. a Smartphone, a tablet, etc.) to provide the acceleration sensory data to the intermediate device(s) which may relay the acceleration sensory data to the remote platform(s) and/or the remote service(s).

As shown at 102, the process 100 starts with the activity detector 220 obtaining the acceleration sensory data from the acceleration sensor(s) 230 during each of a plurality of consecutive basic time intervals.

An activity period may be defined as a sliding window which includes a predefined number of basic time intervals such that the activity period may advance in time to include an additional new time interval while discarding an earliest time interval from the activity period. For example, assuming, the basic time intervals are predefined for a time period of 2-4 seconds, the activity period may be predefined to include 5-10 time intervals such that the duration of the activity period may be, for example, 20-30 seconds.

During each time interval, the activity detector 220 may therefore obtain the acceleration sensory data comprising acceleration measurements, for example, acceleration, deceleration, angular velocity, velocity, angular direction and/or the like of the user(s) 240 and/or one or more parts thereof captured during the respective time interval. Naturally, location information relating to each of the acceleration sensor(s) 230, for example, an attachment mode (e.g. body, head, right hand, left hand, right leg, left leg, etc.), an attachment location (e.g. wrist, arm, ankle, upper body portion, forehead, etc.) and/or the like is available to the activity detector 220.

As shown at 104, the activity detector 220 computes an action score for one or more continuous physical action performed by the user(s) 240 during the respective time interval based on analysis of the received acceleration sensory data. The continuous basic continuous physical actions may be defined as prolonged, long term physical actions extending over a plurality of basic time intervals. Optionally, the continuous basic continuous physical actions may be extend over multiple consecutive basic time intervals. Each of the continuous physical actions may be indicated and/or inferred by one or more respective repetitive motion patterns typical of the respective continuous physical action. The activity detector 220 may therefore analyze the acceleration sensory data to identify one or more of the repetitive motion patterns. The activity detector 220 may compute the action score according to an accuracy of the detection, i.e. a confidence level that the identified basic action is the action the user 240 actually performed in reality. In particular, the confidence level may indicate the confidence in the detection of the repetitive motion pattern(s) indicative of the identified basic action as well as the confidence level in inferring the correct basic action from the detected repetitive motion pattern(s).

For example, assuming a certain acceleration sensor 230 is attached to the upper body part (e.g. chest, shirt, etc.) of a certain user 240, analyzing the acceleration sensory data received from the certain acceleration sensor 230, the activity detector 220 may detect a repetitive minor movement motion pattern in which the upper part of the certain user 240 moves at a significantly stable height while presenting minor back and forth and/or sideways movements. The activity detector 220 may identify the repetitive minor movement motion pattern as indicative of a sitting continuous physical action performed by the certain user 240. In another example, assuming a certain acceleration sensor 230 is attached to a left ankle of a certain user 240, analyzing the acceleration sensory data received from the certain acceleration sensor 230, the activity detector 220 may detect a repetitive back and forth motion pattern. The activity detector 220 may identify the repetitive up and down motion pattern as indicative of a running continuous physical action performed by the certain user 240. In another example relating to the same certain acceleration sensor 230 (left ankle), analyzing the acceleration sensory data received from the certain acceleration sensor 230, the activity detector 220 may detect a repetitive upward motion pattern in which the acceleration measurements depict a rising vector of the left foot. The activity detector 220 may identify the repetitive upward motion pattern as indicative of an upward stairs climbing continuous physical action performed by the certain user 240.

The activity detector 220 may use one or more machine learning activity detection algorithms as known in the art, for example, a decision tree, a neural network, a random forest, an SVM and/or the like to analyze the obtained acceleration sensory data and identify the continuous physical action(s) based on the detected repetitive motion pattern(s). The activity detection algorithm(s) may perform segmentation, feature extraction and classification of the acceleration sensory data and/or motion pattern(s) as known in the art to identify the basic continuous physical action(s) of the user(s) 240. The activity detection algorithm(s) may be trained with one or more training datasets depicting the basic continuous physical action(s) for a plurality of users such as the user 240. For example, the activity detection algorithm(s) may be trained with acceleration sensory data captured during a plurality of sessions, for example, eating, walking, running, working, cooking and/or the like of a plurality of users 240.

The activity detector 220 may assign a probability value to each of the identified basic continuous physical action(s) reflecting a confidence level of the detection of the associated basic continuous physical action(s). Typically, the probability value is associated with the respective basic continuous physical action by the activity detection algorithm(s).

As shown at 106, the activity detector 220 computes a gesture score for one or more brief gestures performed by the user(s) 240 during the respective time interval based on analysis of the received acceleration sensory data. The brief gestures may be defined as short term physical action performed by the user(s) 240 with their hand(s), leg(s) and/or head and may typically be bounded within a single basic time interval, for example, 1-3 seconds. However, the same brief gesture may be repeated multiple times during the activity period. The brief gesture may include, for example, a handshake, raising a glass, lifting a load, cutting a piece of food and/or the like. The activity detector 220 may therefore analyze the acceleration sensory data to identify one or more of the brief gestures. The activity detector 220 may compute the gesture score according to an accuracy of the detection, i.e. a confidence level that the identified gesture is the gesture the user 240 actually performed in reality. For example, assuming a certain acceleration sensor 230 is attached to a left wrist of a certain user 240, analyzing the acceleration sensory data received from the certain acceleration sensor 230, the activity detector 220 may detect a rising and/or falling hand gesture in which the left hand of the certain user 240 moves up and/or down from approximately chest height to face height. The activity detector 220 may identify the rising and/or falling hand gesture as raising a glass gesture, lifting a fork gesture and/or the like performed by the certain user 240.

The activity detector 220 may use one or more machine learning gesture detection algorithms as known in the art, for example, an HMM, a neural network, a decision tree, a random forest, an SVM and/or the like to analyze the obtained acceleration sensory data and identify the gesture. The gesture detection algorithm(s) may perform segmentation, feature extraction and classification of the acceleration sensory data and/or motion pattern(s) as known in the art to identify the gesture(s) of the user(s) 240. The gesture detection algorithm(s) may be trained with one or more training datasets depicting the brief gestures performed by a plurality of users such as the user 240. For example, the activity detection algorithm(s) may be trained with acceleration sensory data captured during a plurality of gesture acts, for example, hand raising, glass raising, fork lifting, writing, hand shaking and/or the like of a plurality of users 240.

The activity detector 220 may assign a probability value to each of the identified brief gestures reflecting a confidence level of the detection of the associated brief gesture(s). Typically, the probability value is associated with the respective brief gesture by the gesture detection algorithm(s).

Optionally, the basic time intervals used by the activity detector 220 to identify the continuous basic continuous physical actions have a different duration than the basic time intervals used by the activity detector 220 to identify the gestures.

As shown at 108, the activity detector 220 aggregates the computed action score(s) and the computed gesture score(s) to produce an interval activity score for one or more predefined complex activities performed by the user(s) 240. The activity detector 220 may typically use the probability value associated with each of the detected basic continuous physical action(s) and gestures to compute the interval activity score. For example, the activity detector 220 may count the number of detections (occurrences) of each of the identified basic continuous physical action(s) and/or brief gestures relating to each predefined complex activity(s) to compute the respective interval activity score(s).

Continuing a previously presented example, assuming a certain action score is computed for the sitting continuous action and a certain gesture score was computed for the fork lifting gesture and/or the glass raising gesture, the activity detector 220 may aggregate the certain action score and the certain gesture score to produce (compute) an activity score for an eating complex activity. The activity score reflects the estimation that the certain user 240 is currently eating.

The activity detector 220 may apply an aggregation algorithm for aggregating the action score(s) and the gesture score(s) to produce the interval activity score for the predefined complex activity(s) performed by the user(s) 240. The aggregation algorithm may employ one or more machine learning methods, techniques and/or algorithms which are trained to compute the interval activity score for the predefined complex activity(s). The training dataset used to train the aggregation algorithm may include a plurality of sets of action score(s) and gesture score(s) where each of the sets may be associated with a label indicating one of the predefined complex activity(s).

Optionally, the activity detector 220 assigns a weight to the probability value associated with one or more of the detected basic continuous physical action(s) and/or gestures to increase the contribution of high probability detection(s) over lower probability detection(s). For example, the activity detector 220 may assign a weight of 1 to activity score(s) and/or gesture score(s) having a detection probability value lower than 95% while assigning a weight of 2 to activity score(s) and/or gesture score(s) having a detection probability value higher than 95%.

As shown at 110, the activity detector 220 adds, for example, combines, sums, aggregates and/or the like the computed interval activity score of each detected complex activity(s) to a respective cumulative activity score computed and accumulated for the respective complex activity during the previous time intervals of the activity period. Thus, each cumulative activity score reflects the activity score of the respective complex activity for the entire activity period and the activity detector 220 therefore updates the cumulative activity score(s) of each of the detected complex activity(s) with the activity score computed during the current time interval. In the steady state where each activity period already includes the predefined number of basic time intervals (applicable to all activity periods except the first few), when adding the interval activity score of the current time interval, the activity detector 220 discards the interval activity score of the earliest time interval of the activity period. Naturally, assuming the interval activity score is adjusted with the probability values, the cumulative activity score inherently reflects the probability adjustment, i.e. the confidence level in the detection of the respective complex activity the user 240 is estimated to be involved in.

An exemplary implementation of the process 100 conducted by the activity detector 220 may be expressed as follows. Assuming a certain complex activity may be characterized by I basic continuous physical actions and J brief gestures. Let $S_A(i,c)$, $1 \le i \le I$, $0 < c \le 1$ denote the activity score of a basic continuous physical action i, $1 \le i \le I$, assigned with a probability value (confidence level) c. The probability values may be weighted such that the activity score may be equal 1 For example, $S_A(i,c)=1$ for $c \le 0.95$, and to $S_A(i,c)=2$ for $0.95 < c \le 1$. Similarly, let $S_G(j,c)$, $1 \le j \le J$, $0 < c \le 1$ denote the gesture score of a certain brief gesture j, $1 \le j \le J$, assigned with a probability value (confidence level) c. Let $A_i$, $1 \le i \le I$, denote the number of detections of the basic continuous physical action i during the activity period, i.e. the sliding window W and $C_{ik}^A$, $1 \le k \le A_i$ denote corresponding probability values. Let $G_j$, $1 \le j \le J$, denote number of detections of the brief gesture j and $C_{jk}^G$, $1 \le j \le G_j$ denote corresponding probability values. The cumulative activity score may thus be presented by equation 1 below.

$$\Sigma_{i=1}^{I} \Sigma_{k=1}^{A_i} S_A(i, C_{ik}^A) + \Sigma_{j=1}^{J} \Sigma_{k=1}^{G_j} S_G(j, C_{jk}^G) \qquad \text{Equation 1:}$$

Continuing the previously presented example, the cumulative activity score may present the number of occurrences of detection of the repetitive motion indicative of the arm lifting action and the number of occurrences of detection of the fork lifting gesture and/or glass raising gesture.

As shown at 112, which is a condition step, the activity detector 220 compares the cumulative activity score of each of the identified complex activity(s) to a predefined threshold. Since each of the predefined complex activities is predefined to comprise a set of one or more certain basic continuous physical actions and one or more certain brief gestures, the activity detector 220 may compare the cumulative activity score reflecting the set of certain basic continuous physical action(s) and certain brief gesture(s) to the predefined threshold. In case the cumulative activity score exceeds the predefined threshold the activity detector 220 branches to step 114, otherwise the activity detector 220 branches back to step 102 and repeats the process 100 for the succeeding basic time interval, i.e. sliding the window of the activity period ahead.

To continue the exemplary implementation presented herein above, let T denote the predefined threshold for detection of the certain complex activity. Formulation of the condition of step 112 may be expressed by equation 2 below, where in case the cumulative activity score exceeds the predefined threshold the activity detector 220 branches to step 114.

$$\Sigma_{i=1}^{I} \Sigma_{k=1}^{A_i} S_A(i, C_{ik}^A) + \Sigma_{j=1}^{J} \Sigma_{k=1}^{G_j} S_G(j, C_{jk}^G) \ge T. \qquad \text{Equation 2:}$$

Continuing the previously presented example, in case the number of occurrences of detection of the repetitive motion indicative of the arm lifting action and the number of occurrences of detection of the fork lifting gesture and/or glass raising gesture exceed a predefined threshold associated with the predefined eating complex activity, the activity detector 220 may estimate the certain user 240 is currently eating.

As shown at 114, the activity detector 220 identifies the predefined complex activity(s) having their respective computed cumulative activity score exceeding the predefined threshold. Following the identification of a certain predefined complex activity, the process 100 may be started again for the certain predefined complex activity after resetting (setting to zero) the cumulative activity score computed for the certain predefined complex activity in order to start accumulating the cumulative activity score from the beginning after removing the contribution of the already identified certain predefined complex activity.

Optionally, the activity detector 220 may be configured to generate a detection indication, alert, message and/or the like to one or more users and/or automated systems.

It is expected that during the life of a patent maturing from this application many relevant systems, methods and computer programs will be developed and the scope of the terms inertial sensor, physical activity detection algorithm, gesture detection algorithm are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The word "exemplary" is used herein to mean "serving as an example, an instance or an illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method of detecting complex user activities comprising a plurality of continuous physical actions and brief gestures, comprising:
   using at least one processor in each of a plurality of consecutive time intervals for:
      obtaining sensory data from at least one wearable inertial sensor worn by a user;
      computing an action score for at least one continuous physical action performed by said user, said at least one continuous physical action extends over multiple consecutive basic time intervals and is indicated by at least one repetitive motion pattern identified by analyzing said sensory data;
      computing a gesture score for at least one brief gesture performed by said user, said at least one brief gesture is bounded in a single basic time interval and is identified by analyzing said sensory data;
      aggregating said action score and said gesture score to produce an interval activity score of at least one predefined activity of said user for a respective one of said plurality of consecutive time intervals;
      adding said interval activity score to a cumulative activity score of said at least one predefined activity accumulated during a predefined number of preceding time intervals of said plurality of consecutive time intervals; and
      identifying said at least one predefined activity when said cumulative activity score exceeds a predefined threshold.

2. The computer implemented method of claim 1, wherein said at least one wearable inertial sensor is an accelerometer located and configured to measure an acceleration of at least one member of a group consisting of: said user, a head of said user and at least one limb of said user.

3. The computer implemented method of claim 1, wherein said at least one wearable inertial sensor is a gyroscope located and configured to measure an angular velocity of at least one member of a group consisting of: said user, a head of said user and at least one limb of said user.

4. The computer implemented method of claim 1, wherein said at least one continuous physical action is identified using at least one action detection algorithm, said at least one action detection algorithm implements a decision tree algorithm.

5. The computer implemented method of claim 4, wherein said at least one action detection algorithm is trained with a training dataset relating to said at least one continuous physical action.

6. The computer implemented method of claim 1, wherein said action score is computed according to an action probability value associated with said at least one continuous physical action.

7. The computer implemented method of claim 6, further comprising assigning a weight to said action probability value for computing said action score.

8. The computer implemented method of claim 1, wherein said at least one brief gesture is identified using at least one gesture detection algorithm, said at least one gesture detection algorithm implements a Hidden Markov Model (HMM) algorithm.

9. The computer implemented method of claim 8, wherein said at least one gesture detection algorithm is trained with a training dataset relating to said at least one brief gesture.

10. The computer implemented method of claim 1, wherein said gesture score is computed according to a gesture probability value associated with said at least one brief gesture.

11. The computer implemented method of claim 10, further comprising assigning a weight to said gesture probability value for computing said gesture score.

12. The computer implemented method of claim 1, wherein said plurality of consecutive time intervals form an activity period implementing a sliding time window in which after each time interval a new time interval is added to said activity period and an earliest time interval is discarded from said activity period.

13. The computer implemented method of claim 1, wherein said cumulative activity score is reset in case said predefined activity is identified.

14. A system for detecting complex user activities comprising a plurality of continuous physical actions and brief gestures, comprising:
   at least one processor adapted to execute code in each of a plurality of consecutive time intervals, the code comprising:
      code instructions to obtain sensory data from at least one wearable inertial sensor worn by a user;
      code instructions to compute an action score for at least one continuous physical action performed by said user, said at least one continuous physical action extends over multiple consecutive basic time intervals and is indicated by at least one repetitive motion pattern identified by analyzing said sensory data;
      code instructions to compute a gesture score for at least one brief gesture performed by said user, said at least one brief gesture is bounded in a single basic time interval and is identified by analyzing said sensory data;

code instructions to aggregate said action score and said gesture score to produce an interval activity score of at least one predefined activity of said user for a respective one of said plurality of consecutive time intervals;

code instructions to add said interval activity score to a cumulative activity score of said at least one predefined activity accumulated during a predefined number of preceding time intervals of said plurality of consecutive time intervals; and code instructions to identify said at least one predefined activity when said cumulative activity score exceeds a predefined threshold.

15. A computer program product for detecting complex user activities comprising a plurality of continuous physical actions and brief gestures, comprising:

a non-transitory computer readable storage medium storing a program that causes a computer to execute code in each of a plurality of consecutive time intervals;

first code instructions for obtaining sensory data from at least one wearable inertial sensor worn by a user;

second code instructions for computing an action score for at least one continuous physical action performed by said user, said at least one continuous physical action extends over multiple consecutive basic time intervals and is indicated by at least one repetitive motion pattern identified by analyzing said sensory data;

third code instructions for computing a gesture score for at least one brief gesture performed by said user, said at least one brief gesture is bounded in a single basic time interval and is identified by analyzing said sensory data;

fourth code instructions for aggregating said action score and said gesture score to produce an interval activity score of at least one predefined activity of said user for a respective one of said plurality of consecutive time intervals;

fifth code instructions for adding said interval activity score to a cumulative activity score of said at least one predefined activity accumulated during a predefined number of preceding time intervals of said plurality of consecutive time intervals; and sixth code instructions for identifying said at least one predefined activity when said cumulative activity score exceeds a predefined threshold;

wherein said first, second, third, fourth, fifth and sixth program instructions are executed by at least one processor from said non-transitory computer readable storage medium.

* * * * *